(12) United States Patent
Goto et al.

(10) Patent No.: US 10,398,404 B2
(45) Date of Patent: Sep. 3, 2019

(54) DATA PROCESSING DEVICE, X-RAY CT APPARATUS, AND REFERENCE CORRECTION METHOD

(71) Applicant: HITACHI, LTD., Tokyo (JP)

(72) Inventors: Taiga Goto, Tokyo (JP); Hisashi Takahashi, Tokyo (JP); Koichi Hirokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 396 days.

(21) Appl. No.: 15/509,115

(22) PCT Filed: Oct. 7, 2015

(86) PCT No.: PCT/JP2015/078466
§ 371 (c)(1),
(2) Date: Mar. 6, 2017

(87) PCT Pub. No.: WO2016/063725
PCT Pub. Date: Apr. 28, 2016

(65) Prior Publication Data
US 2017/0273657 A1    Sep. 28, 2017

(30) Foreign Application Priority Data

Oct. 22, 2014   (JP) .................................. 2014-215112

(51) Int. Cl.
*A61B 6/03* (2006.01)
*A61B 6/00* (2006.01)

(52) U.S. Cl.
CPC .............. *A61B 6/582* (2013.01); *A61B 6/032* (2013.01); *A61B 6/488* (2013.01); *A61B 6/5205* (2013.01);
(Continued)

(58) Field of Classification Search
CPC .. A61B 6/03; A61B 6/032; A61B 6/52; A61B 6/5258; A61B 6/5294; A61B 6/58; A61B 6/582
See application file for complete search history.

(56) References Cited

U.S. PATENT DOCUMENTS 5,761,257 A    6/1998  Toth et al.
6,996,206 B2 *  2/2006  Hsieh ..................... A61B 6/032
                                                   378/19
(Continued)

FOREIGN PATENT DOCUMENTS

JP    1-310644    12/1989
JP    10-225453   8/1998

OTHER PUBLICATIONS

International Search Report in connection with PCT/JP2015/078466.

*Primary Examiner* — Thomas R Artman
(74) *Attorney, Agent, or Firm* — Cooper & Dunham LLP

(57) ABSTRACT

In order to provide a data processing device and the like, capable of performing highly accurate reference correction even in a case where an object protrudes in reference channels in most of the measurement views, an image processing device (data processing device) of an X-ray CT apparatus calculates a unit air calibration reference value which is a value per unit tube current of an air calibration reference value which is reference data measured during air calibration, calculates a reference value (estimated reference value) corresponding to an X-ray condition in the main scanning on the basis of an output tube current value in the main scanning and a unit air calibration reference value, and corrects normalized reference data obtained by normalizing a measured reference value in the main scanning with the
(Continued)

estimated reference value, to be included in an allowable error range, so as to remove the influence of protrusion.

8 Claims, 9 Drawing Sheets

(52) U.S. Cl.
CPC .......... *A61B 6/5258* (2013.01); *A61B 6/5294* (2013.01); *A61B 6/585* (2013.01)

(56) References Cited

U.S. PATENT DOCUMENTS

| | | | |
|---|---|---|---|
| 9,268,046 B2 * | 2/2016 | Carmi | G01N 23/046 |
| 2005/0226366 A1 * | 10/2005 | Hsieh | A61B 6/032 |
| | | | 378/16 |
| 2014/0140469 A1 * | 5/2014 | Carmi | G01N 23/046 |
| | | | 378/9 |
| 2017/0273657 A1 * | 9/2017 | Goto | A61B 6/032 |

* cited by examiner

FIG.3
(a)
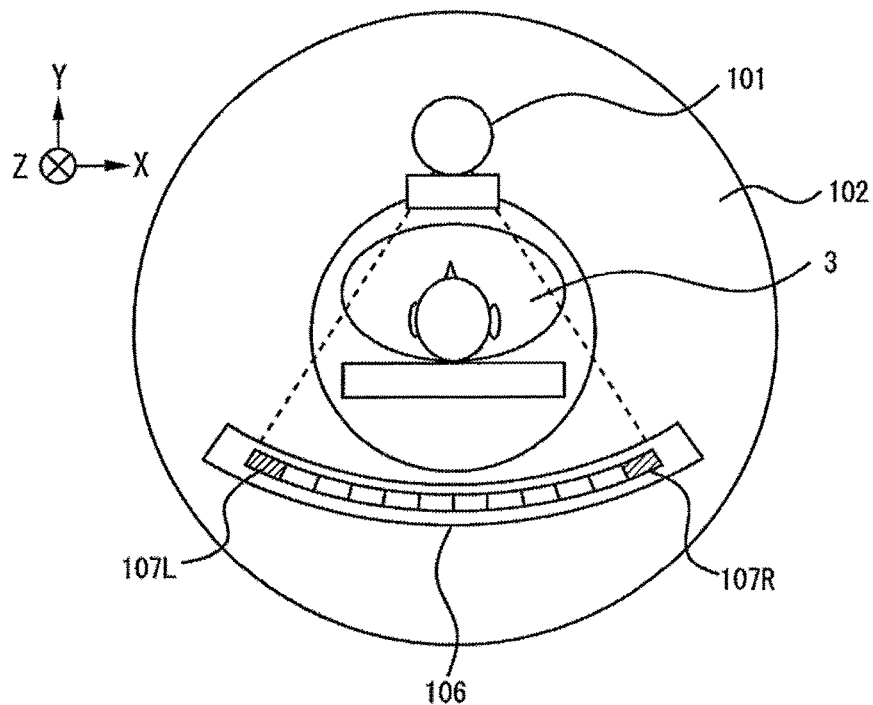
(b)
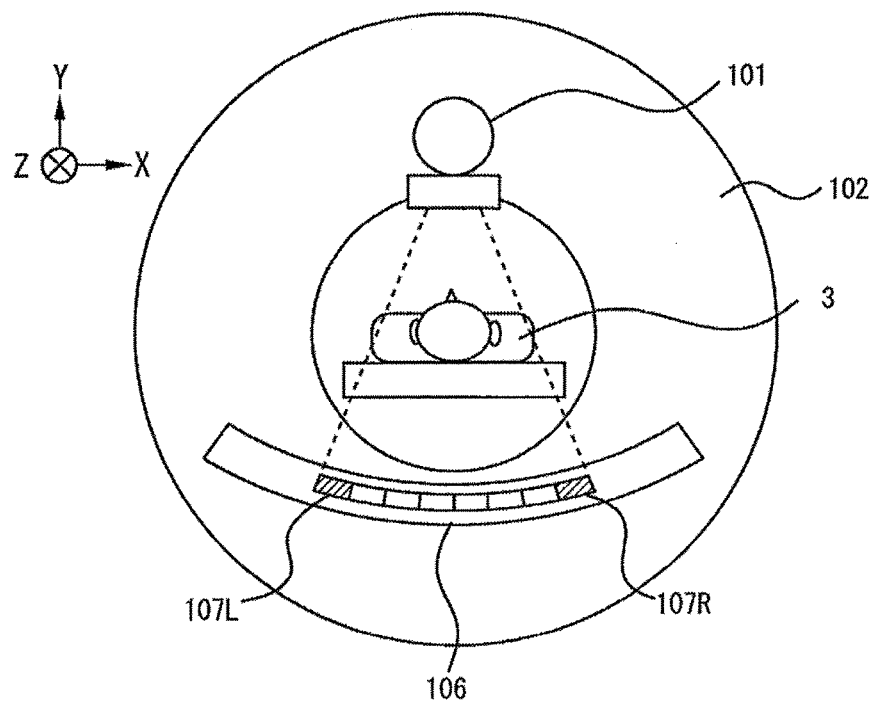

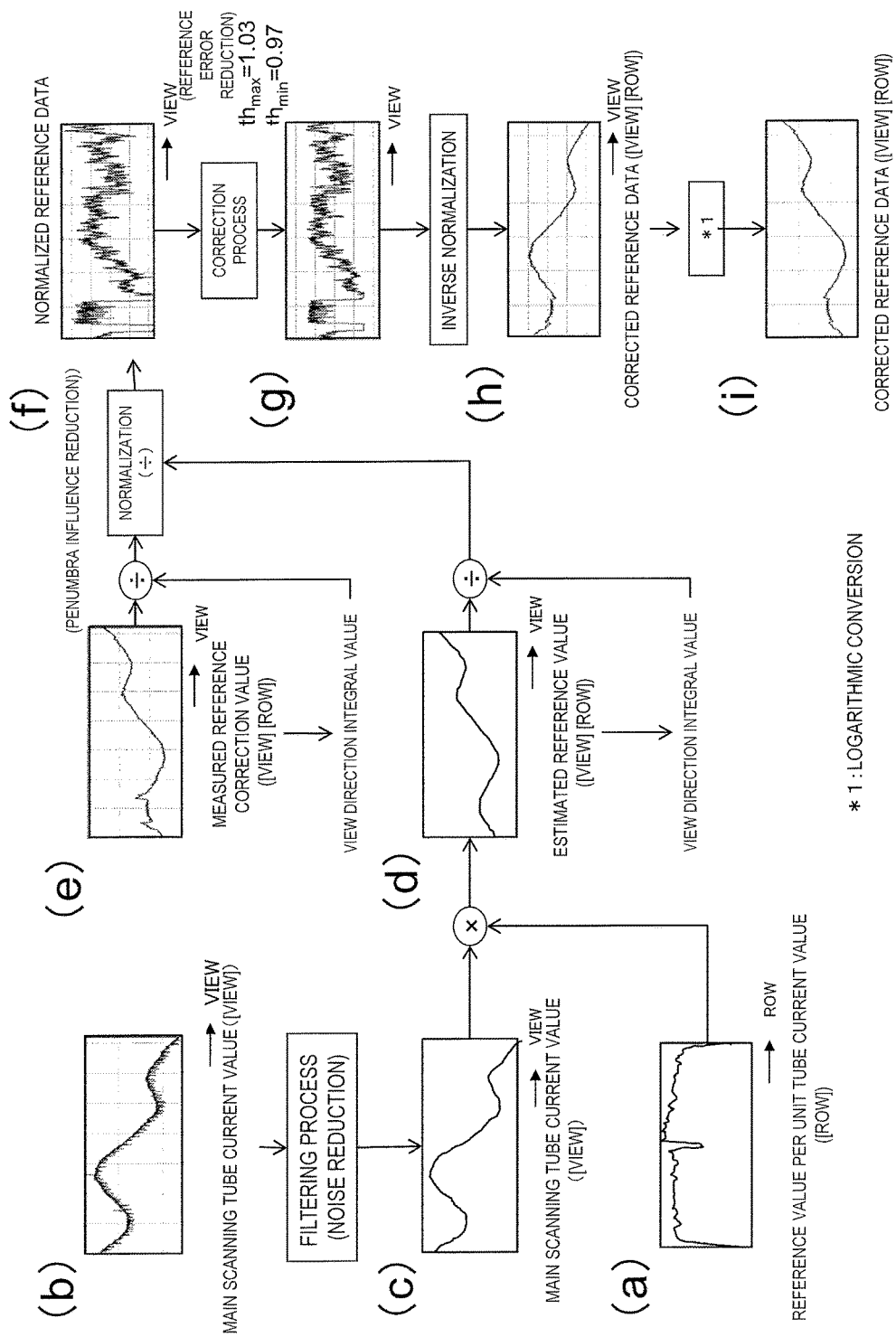

DATA PROCESSING DEVICE, X-RAY CT APPARATUS, AND REFERENCE CORRECTION METHOD

TECHNICAL FIELD

The present invention relates to a data processing device, an X-ray CT apparatus, and a reference correction method, and particularly to reference correction on measured data obtained by an X-ray CT apparatus.

BACKGROUND ART

An X-ray CT apparatus is an apparatus which applies X-rays from the periphery of an object, collects data regarding the intensity of X-rays transmitted through the object by using an X-ray detector, and generates, as an image, information regarding a distribution of an X-ray absorption coefficient of the inside of the object on the basis of the collected data. The intensity or ray quality (spectral distribution) of X-rays radiated from an X-ray source of the X-ray CT apparatus temporally changes. In order to compensate for the temporal change, reference correction is performed on data measured by the X-ray detector.

In the reference correction, generally, one to a plurality of detection element channels at both ends of the X-ray detector are used as calibration detection elements (hereinafter, referred to as reference detectors), and X-rays which are not transmitted through an object are directly detected by the reference detectors. An image processing device (data processing device) of the X-ray CT apparatus calibrates X-ray intensity levels obtained by other channels with an X-ray intensity detected by the reference detectors as a reference, and generates an image such as a tomographic image by using a calibrated signal.

However, for example, in a case where a physique of an object is large, or a case where an object is disposed to be deviated from the rotation center of a scanner, a normal reference signal may not be obtained since X-rays incident to the reference detectors are blocked by the object. In order to solve such a problem caused by protrusion of an object, signals obtained from the reference detectors at both ends are compared with a predetermined threshold value, and it is determined whether or not the reference detectors are shielded on the basis of the magnitude of a signal intensity. In a case where one of the reference detectors is shielded, an artifact is prevented from becoming apparent by using only a signal from the other reference detector as reference correction data.

PTL 1 discloses a method in which output data from each of reference detectors at both ends is monitored in each measurement view, the maximum signal value up to the previous view of a view which is a calculation target is held, protrusion is determined in a case where the output data is less than a predetermined threshold value, and measured data in which protrusion occurs is replaced in the maximum signal value up to views before the protrusion occurs. According to this method, even in a case where reference channels at both ends are shielded, reference correction is appropriately performed.

Meanwhile, in recent years, it has been frequently performed to scan a relatively large object as exemplified by metabolic syndrome. There is a bed which is horizontally movable in a state in which an object is placed on the bed, and the bed may protrude out of a field of view (FOV). From this background, it is necessary to correct protrusion with high accuracy even in a case where protrusion occurs in most of the measurement views during scanning. In order to improve the accuracy of reference correction, it is preferable to perform correction by using an X-ray output change component in real time during main scanning.

CITATION LIST

Patent Literature

PTL 1: JP-A-2003-144427

SUMMARY OF INVENTION

Technical Problem

However, in the method disclosed in PTL 1, since measured values up to the previous view of a view in which protrusion occurs are used, correction cannot be performed in a case where protrusion occurs from right after scanning starts. Since data is replaced with data regarding a measurement view in which protrusion does not occur, the data is not normalized with an X-ray output change component in real time.

The present invention has been made in consideration of the above-described problems, and an object thereof is to provide a data processing device, an X-ray CT apparatus, and a reference correction method, capable of performing highly accurate reference correction even in a case where an object protrudes in reference channels in most of the measurement views.

Solution to Problem

In order to achieve the above-described object, according to a first invention, there is provided a data processing device including a unit air calibration reference value calculation unit that calculates a unit air calibration reference value which is a value per unit tube current of an air calibration reference value which is reference data measured during air calibration; a tube current value acquisition unit that acquires an output tube current value in main scanning; an estimated reference value calculation unit that calculates an estimated reference value which is a reference value corresponding to an X-ray condition in the main scanning on the basis of the unit air calibration reference value and the output tube current value in the main scanning; a normalization unit that normalizes a measured reference value which is a reference value measured in the main scanning with the estimated reference value, so as to calculate normalized reference data; a correction processing unit that corrects the normalized reference data to be included in an allowable error range; an inverse normalization unit that inversely normalizes the corrected normalized reference data with the estimated reference value so as to obtain corrected reference data; and a reference correction unit that acquires measured data which is measured in the main scanning and performs reference correction on the measured data by using the corrected reference data.

According to a second invention, there is provided an X-ray CT apparatus including the data processing device according to the first invention.

According to a third invention, there is provided a reference correction method including causing a data processing device to perform a step of calculating a unit air calibration reference value which is a value per unit tube current of an air calibration reference value which is reference data measured during air calibration; a step of acquiring an output tube current value in main scanning; a step of calculating an estimated reference value which is a reference value corresponding to an X-ray condition in the main scanning on the basis of the unit air calibration reference value and the output tube current value in the main scanning; a step of normalizing a measured reference value which is a reference value measured in the main scanning with the estimated reference value, so as to calculate normalized reference data; a step of correcting the normalized reference data to be included in an allowable error range; a step of inversely normalizing the corrected normalized reference data with the estimated reference value so as to obtain corrected, reference data; and a step of acquiring measured data which is measured in the main scanning and performing reference correction on the measured data by using the corrected reference data.

According to a fourth invention, there is provided a data processing device including a unit air calibration reference value calculation unit that calculates a unit air calibration reference value which is a value per unit tube current of an air calibration reference value which is reference data measured during air calibration; a tube current value acquisition unit that acquires an output tube current value in main scanning; an estimated reference value calculation unit that calculates an estimated reference value which is a reference value corresponding to an X-ray condition in the main scanning on the basis of the unit air calibration reference value and the output tube current value in the main scanning; and a reference correction unit that acquires measured data which is measured in the main scanning and performs reference correction on the measured data by using the estimated reference value.

Advantageous Effects of Invention

According to the present invention, it is possible to provide a data processing device, an X-ray CT apparatus, and a reference correction method, capable of performing highly accurate reference correction even in a case where an object protrudes in reference channels in most of the measurement views.

BRIEF DESCRIPTION OF DRAWINGS

FIG. 3 is a diagram for explaining X-rays which are incident to the reference detectors and protrusion of an object, in which FIG. 3(a) illustrates a case where the object is large, and FIG. 3(b) illustrates a case where the number of channels of an X-ray detector is small.

FIG. 4 is a diagram illustrating an example of a projection data profile, in which FIG. 4(a) illustrates a case where there is no protrusion, FIG. 4(b) illustrates a case where one side protrudes, and FIG. 4(c) illustrates a case where both sides protrude.

FIG. 9 is a diagram illustrating data profiles in respective steps in the corrected reference data calculation process illustrated in FIG. 8.

DESCRIPTION OF EMBODIMENTS

Hereinafter, embodiments of the present invention will be described in detail with reference to the drawings.

[First Embodiment]

First, an X-ray CT apparatus 1 according to the present invention will be described.

Figure 1:
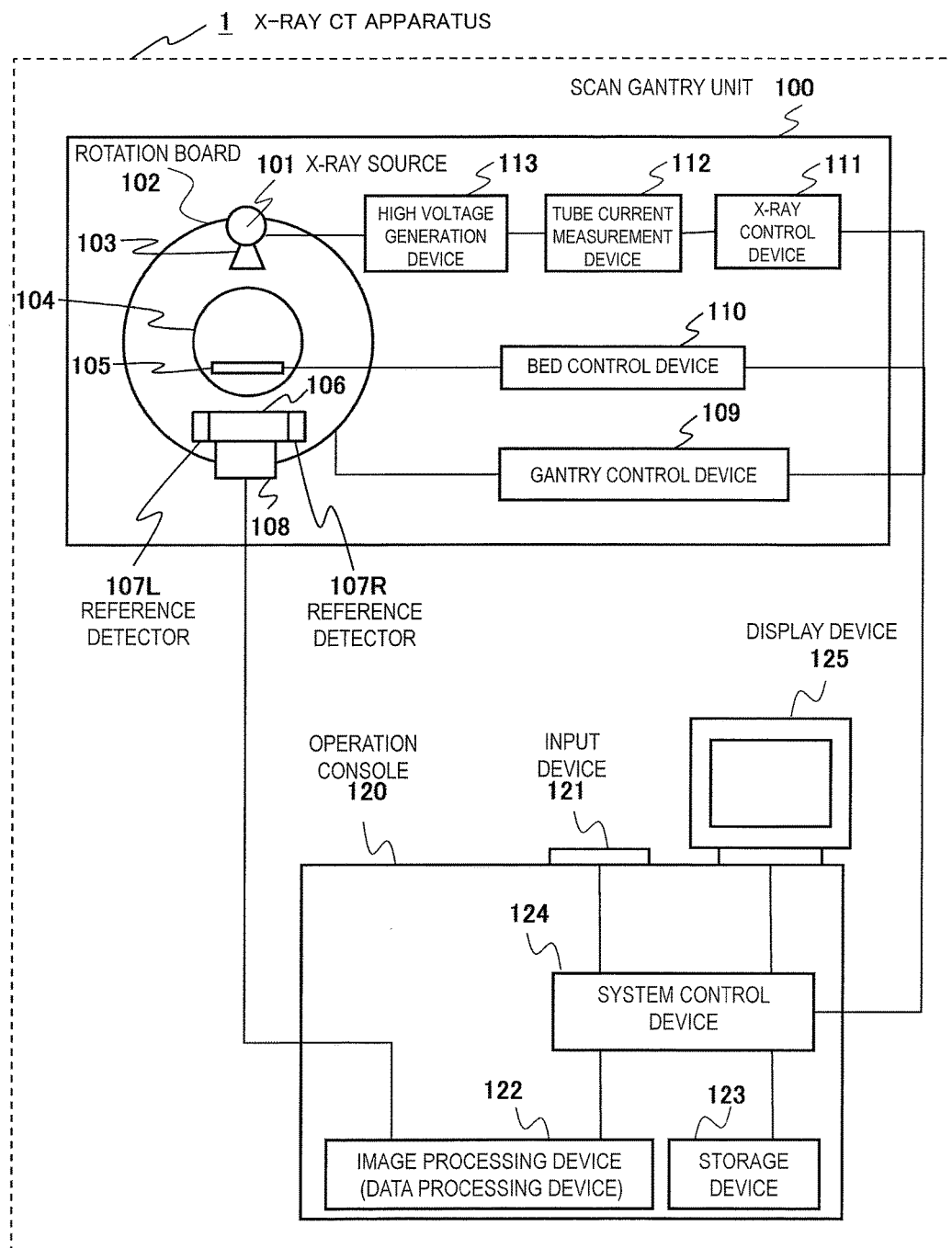
FIG. 1 is the entire configuration diagram of an X-ray CT apparatus 1.

FIG. 1 is a diagram illustrating the entire configuration of the X-ray CT apparatus 1. As illustrated in FIG. 1, the X-ray CT apparatus 1 includes a scan gantry unit 100, a bed 105, and an operation console 120. The scan gantry unit 100 is a device which irradiates an object with X-rays and detects X-rays transmitted through the object. The operation console 120 is a device which controls each constituent element of the scan gantry unit 100, and acquires transmitted X-ray data (measured data) measured by the scan gantry unit 100 so as to generate an image such as an object tomographic image on the basis of the measured data. The bed 105 is a device on which the object is laid and is mounted and which carries the object into and out of an X-ray irradiation range of the scan gantry unit 100.

The scan gantry unit 100 includes an X-ray source 101, a rotation board 102, a collimator 103, an X-ray detector 106, reference detectors 107L and 107R, a data collecting device 108, a gantry control device 109, a bed control device 110, an X-ray control device 111, a tube current measurement device 112, and a high voltage generation device 113.

The operation console 120 includes an input device 121, an image processing device 122, a storage device 123, a system control device 124, and a display device 125.

The rotation board 102 of the scan gantry unit 100 is provided with an opening 104, and the X-ray source 101 and the X-ray detector 106 are disposed to oppose each other with the opening 104 interposed therebetween. An object mounted on the bed 105 is inserted into the opening 104. The rotation board 102 is rotated around the object by driving force which is transmitted from a rotation board driving device via a driving transmission system. The rotation board driving device is controlled by the gantry control device 109.

The X-ray control device 111 sends a control signal based on an X-ray tube voltage value and an X-ray tube current value determined by the system control device 124 of the operation console 120, to the high voltage generation device 113. The high voltage generation device 113 applies and supplies an X-ray tube voltage and an X-ray tube current to the X-ray source 101 in response to the control signal which is input from the X-ray control device 111. The X-ray source 101 continuously or intermittently applies X-rays with the intensity corresponding to the X-ray tube voltage and the X-ray tube current.

In the present embodiment, as illustrated in FIG. 1, the tube current measurement device 112 which monitors a signal output from the X-ray control device 111 is provided. The tube current measurement device 112 measures an X-ray tube current value which is actually supplied to the X-ray source 101 (X-ray tube) during air calibration or main scanning. The system control device 124 is notified of the X-ray tube current value measured by the tube current measurement device 112.

The collimator 103 is provided in an X-ray irradiation outlet of the X-ray source 101. The collimator 103 is a device which restricts an irradiation range of X-rays radiated from the X-ray tube 101, and shapes the X-rays into, for example, a cone beam (a conical or pyramidal beam). An aperture width of the collimator 103 is controlled by the system control device 124.

The X-rays applied from the X-ray source 101 are transmitted through the object and are incident to the X-ray detector 106.

Alternatively, the X-rays are transmitted through only air without being transmitted through the object, and are incident to the X-ray detector 106.

The X-ray detector 106 is disposed to oppose the X-ray source 101, and detects a dose of incident X-rays so as to output the X-ray dose to the data collecting device 108. The X-ray detector 106 is a detector in which, for example, X-ray detection element groups each constituted of a scintillator and a photodiode are two-dimensionally arranged in a channel direction (rotation direction) and a row direction (body axis direction). One or a plurality of channels located at both ends of the X-ray detector 106 are used as channels for acquiring reference data used for reference correction.

Hereinafter, the channels for acquiring reference data will be referred to as reference detectors, a right reference detector is indicated by the reference sign 107R, and a left reference detector is indicated by the reference sign 107L. In a case where the left and right reference detectors 107L and 107R are not required to be differentiated from each other, the reference sign 107 is used. The reference detector 107 measures reference data while being rotated around the object during air calibration and main scanning, and outputs the reference data to the data collecting device 108.

The data collecting device 108 collects an electric signal (current) corresponding to an X-ray dose detected by each X-ray detection element of the X-ray detector 106 at a predetermined sampling interval, amplifies the X-ray dose with a preamplifier, converts the X-ray dose into a digital signal with an A/D converter, and sequentially outputs the digital signal to the image processing device 122 of the operation console 120 as X-ray attenuation data. The reference data obtained by the reference detectors 107 at both ends is also collected at a predetermined sampling interval in the same manner, so as to be converted into a digital signal, and is sequentially output to the image processing device 122 of the operation console 120 as X-ray attenuation data.

The image processing device (data processing device) 122 acquires the X-ray attenuation data which is input from the data collecting device 108, and performs predetermined preprocesses on the X-ray attenuation data so as to generate projection data which is required to reconstruct an image. The preprocesses include a reference correction process, logarithmic conversion, calibration, and the like. The reference correction process may be performed after the X-ray attenuation data is subject to logarithmic conversion, and may be performed before logarithmic conversion. In the present specification, in the first embodiment, a reference correction process performed after logarithmic conversion will be described, and, in the second embodiment, a reference correction process performed before logarithmic conversion will be described.

Here, with reference to FIGS. 2 and 3, reference correction will be described.

The reference correction is to correct a change in an X-ray output. In this reference correction, measured data (X-ray attenuation data) in detector channels other than the reference detectors is normalized by using the X-ray attenuation data obtained by the reference detectors 107, regarding X-rays having passed through only air, and thus an X-ray output change is compensated for, and output levels of the detector channels are calibrated.

In a case where a correction target is X-ray attenuation data (measured data not having undergone logarithmic conversion), as shown in the following Equation (1), normalization is performed by dividing measured data by reference data (reference attenuation data) before logarithmic conversion. In a case where a correction target is projection data (measured data having undergone logarithmic conversion), as shown in the following Equation (2), normalization is performed by subtracting reference data (reference projection data) after logarithmic conversion from projection data.

$$\text{Attenuation data having undergone reference correction} = \text{X-ray attenuation data/reference attenuation data} \quad (1)$$

$$\text{Projection data having undergone reference correction} = \text{projection data} - \text{reference projection data} \quad (2)$$

Figure 2:
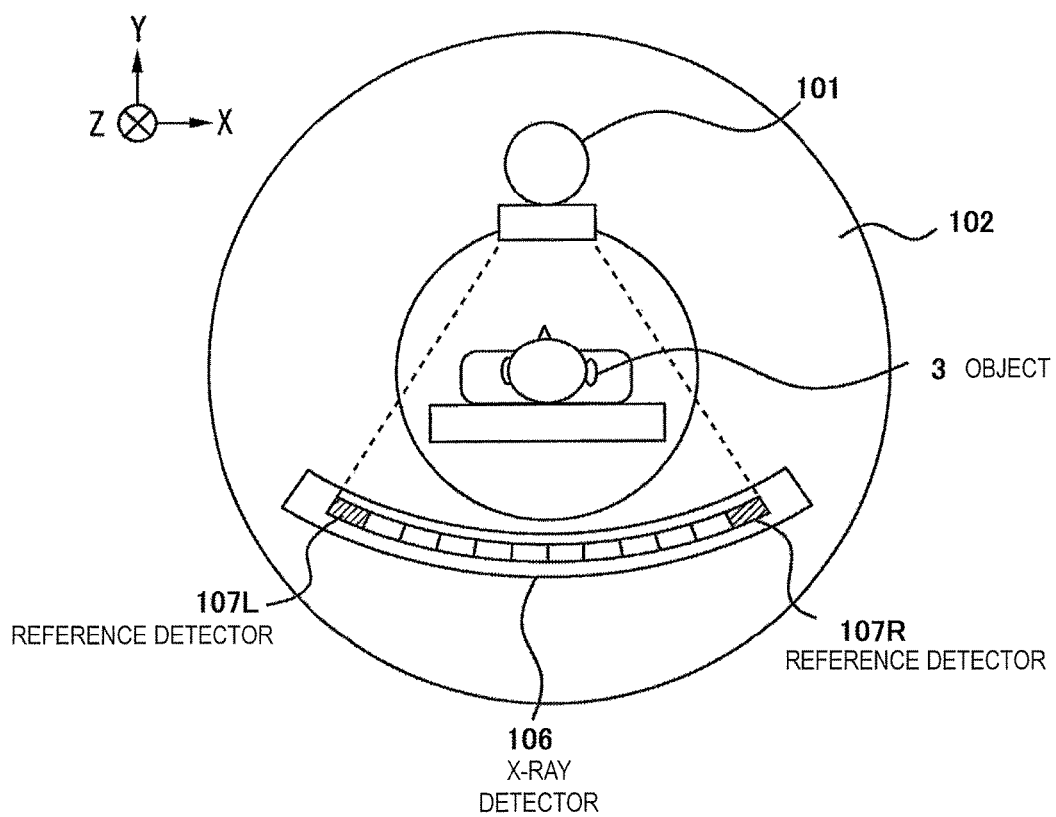
FIG. 2 is a diagram for explaining X-rays which are incident to reference detectors.

FIG. 2 is a diagram illustrating arrangement of the general reference detectors 107. Reference data used for reference correction is required to be X-ray attenuation data regarding X-rays which are not transmitted through an object 3. Therefore, for example, as illustrated in FIG. 2, one or a plurality of channels located at both ends of the X-ray detector 106 are used as the reference detectors 107L and 107R. The reference detectors 107 detect a dose of X-rays having passed through only air. An X-ray filter such as a bow tie filter may be disposed between an X-ray source and an object, but, herein, for simplification of description, the description will be made regardless of the filter assuming that X-rays pass through only air since correction is performed through air calibration.

In a case where the object 3 is very large as illustrated in FIG. 3(a), or in a case where the object 3 is not large but an apparatus has a narrow field of view (FOV) due to a small number of channels of the X-ray detector 106 as illustrated in FIG. 3(b), X-rays having passed through the object 3 are incident to the reference detectors 107. This state is referred to as "protrusion". If reference correction is performed by using reference data obtained in a state in which protrusion occurs, a projection value of the object 3 is not accurately calculated, and, as a result, a CT value of the object 3 is abnormal.

Figure 4:
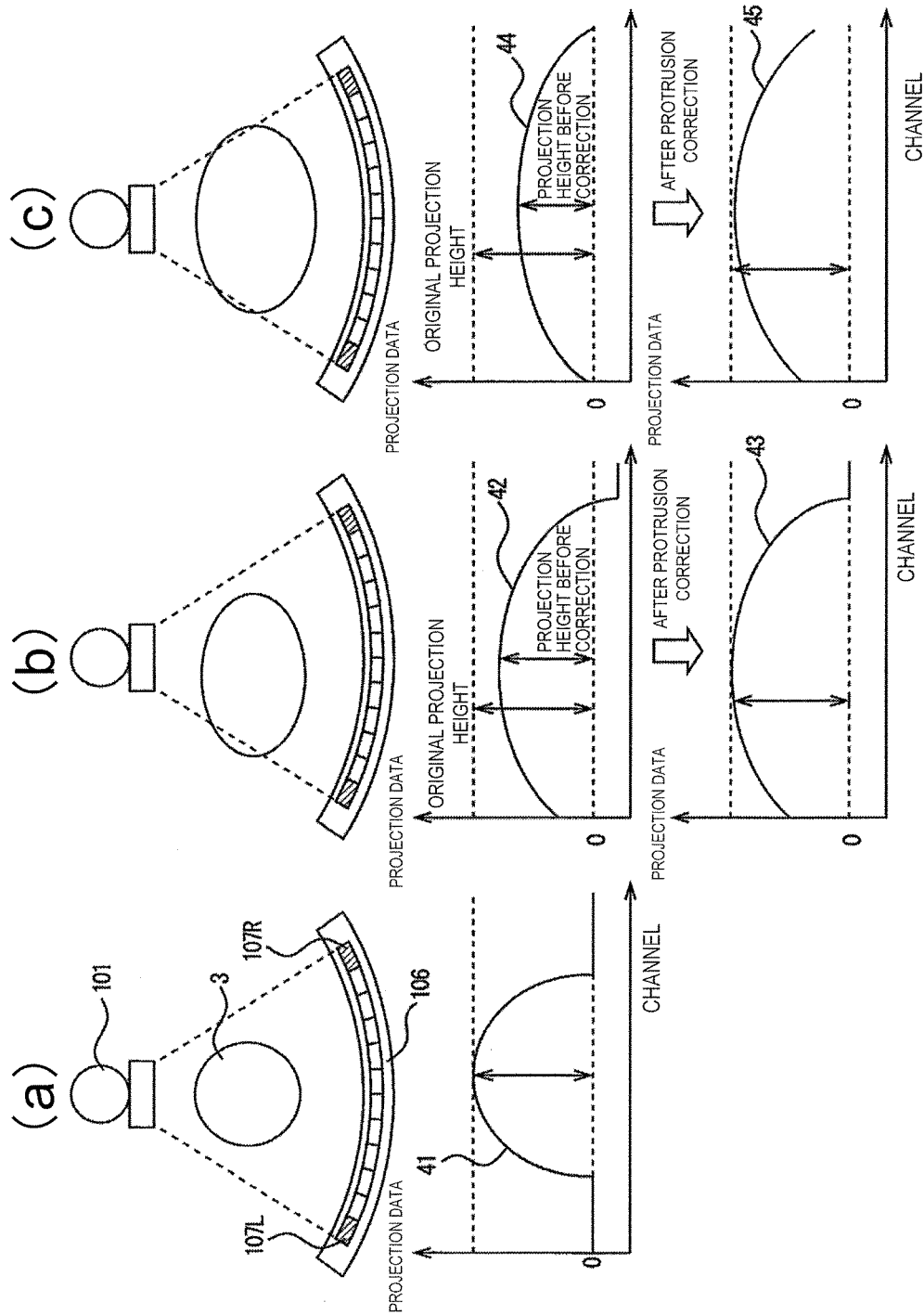

FIG. 4 is a diagram for explaining projection data having undergone reference correction, corresponding to whether or not protrusion is present.

As illustrated in FIG. 4(a), in a case where reference correction is performed by using reference data obtained in a state in which protrusion is not present, as shown in a profile 41, a projection value of the object 3 is corrected so that a projection value of an air portion is "0", and thus accurate projection data having undergone the reference correction can be obtained. However, as illustrated in FIG. 4(b) or 4(c), if reference correction is performed by using reference data obtained in a state in which protrusion is present, projection data having undergone the reference correction is calculated to be lower than an inherent projection height as shown in profiles 42 and 44.

Therefore, the X-ray CT apparatus 1 (image processing device 122) according to the present invention performs a corrected reference data generation process which will be described later, so as to generate corrected reference data from which the influence of protrusion is removed, and performs reference correction by using the corrected reference data. Details of the corrected reference data generation process will be described later.

The image processing device 122 performs preprocesses such as logarithmic conversion, reference correction, and calculation on X-ray attenuation data, so as to generate projection data, and reconstruct an object image such as a tomographic image by using the generated projection data. The system control device 124 stores object image data reconstructed by the image processing device 122 in the storage device 123 and also displays the object image data on the display device 125. The image processing device 122 may preserve X-ray attenuation data which is input from the data collecting device 108 in the storage device 123, and may read the X-ray attenuation data at any timing which is different from the time of scanning so as to perform a projection data generation process.

The system control device 124 is a computer provided with a central processing unit (CPU), a read only memory (ROM), a random access memory (RAM), and the like. The storage device 123 is a data recording device such as a hard disk, and stores in advance programs or data for realizing a function of the X-ray CT apparatus 1.

The display device 125 is formed of a display such as a liquid crystal panel or a CRT monitor, and a display control circuit which displays predetermined display data on the display. The display device 125 displays an object image output from the image processing device 122, and various information treated by the system control device 124.

The input device 121 is formed of, for example, a pointing device such as a keyboard or a mouse, numeric keys, and various switch buttons, and outputs various instructions or information which is input by an operator to the system control device 124. The operator operates the X-ray CT apparatus 1 in an interaction manner by using the display device 125 and the input device 121. The input device 121 may be a touch panel type input device which is integrally formed with a display screen of the display device 125.

The bed 105 is provided with a top plate on which the object 3 is laid and mounted, a vertical moving device, and a top plate driving device. The bed 105 moves the top plate vertically, moves the top plate in a front-and-rear direction along the body axis direction, and moves the top plate in a direction (leftward-and-rightward direction) which is perpendicular to the body axis and is parallel to a floor surface, under the control of the bed control device 110. During scanning, the bed control device 110 moves the top plate according to a bed movement speed and a movement direction determined by the system control device 124.

Next, with reference to FIGS. 5 to 7, an operation of the X-ray CT apparatus 1 will be described.

Figure 5:
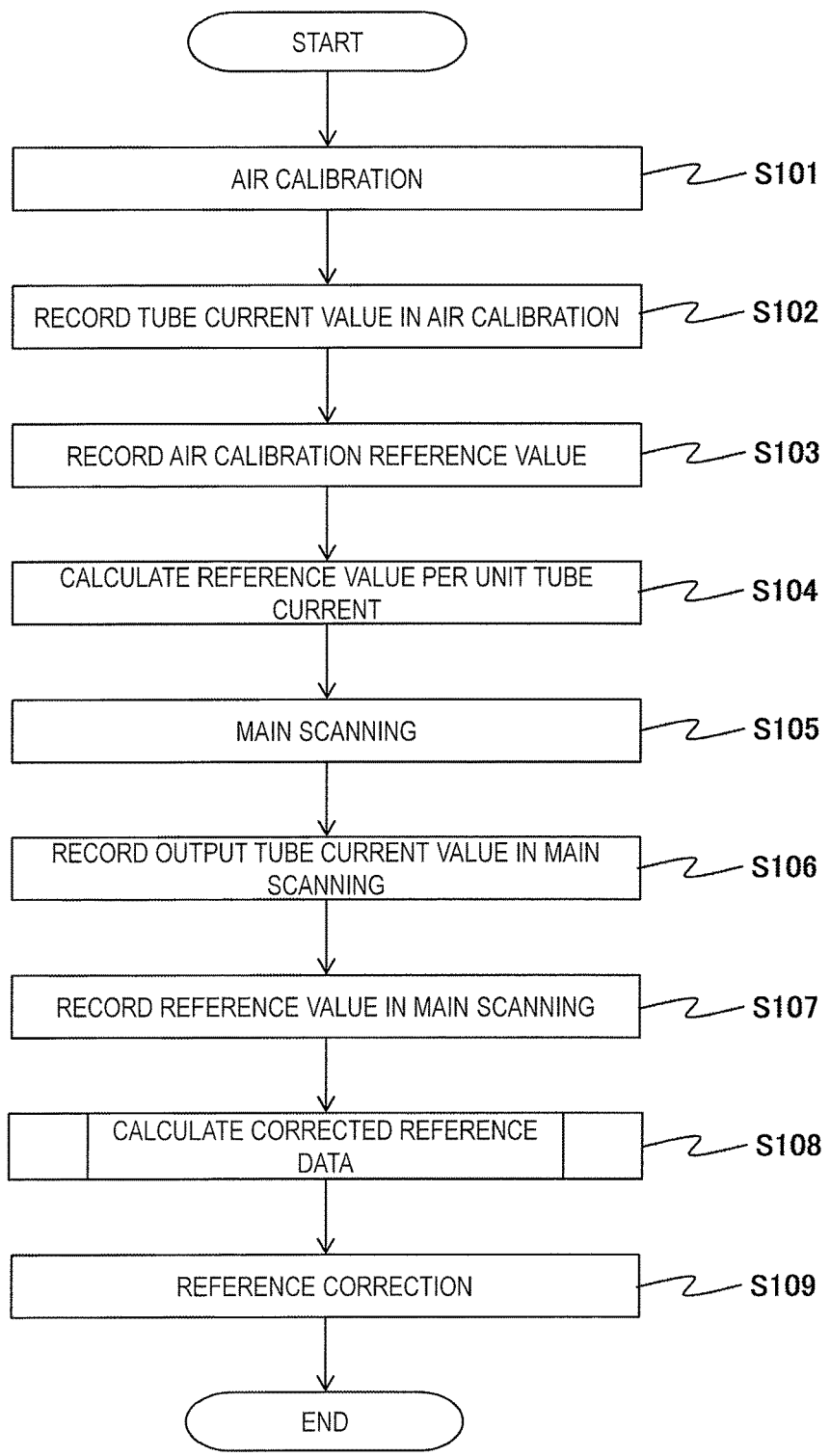
FIG. 5 is a flowchart illustrating processing procedures of the entire projection data generation process.

The image processing device 122 of the X-ray CT apparatus 1 creates projection data according to procedures illustrated in a flowchart of FIG. 5. In the first embodiment, a description will be made of procedures of calculating corrected reference data by using projection data having undergone logarithmic conversion and performing reference correction.

The X-ray CT apparatus 1 first performs air calibration prior to main scanning (step S101). The air calibration is a process in which air scanning is performed in a state in which there is no object, X-ray attenuation data (air data) regarding X-rays having passed through only air, or air and an X-ray filter such as a bow tie filter or a collimator is acquired, and an output level of each detection element is calibrated by using the air data. The system control device 124 measures an output tube current value (air scanning tube current value) during air scanning with the tube current measurement device 112, and holds the air scanning tube current value in the storage device 123 or the like (step S102). The air scanning tube current value is measured throughout all views.

The image processing device 122 acquires X-ray attenuation data measured by the reference detectors 107 in the air scanning, and holds the X-ray attenuation data in the storage device 123 or the like as an air calibration reference value (step S103).

The image processing device 122 acquires the air scanning tube current value recorded in step S102 and the air calibration reference value recorded in step S103, divides the air calibration reference value by the air scanning tube current value for each view so as to calculate a "reference value per unit tube current (1 mA) (unit air calibration reference value)", and holds the unit air calibration reference value in the storage device 123 (step S104).

Figure 6:
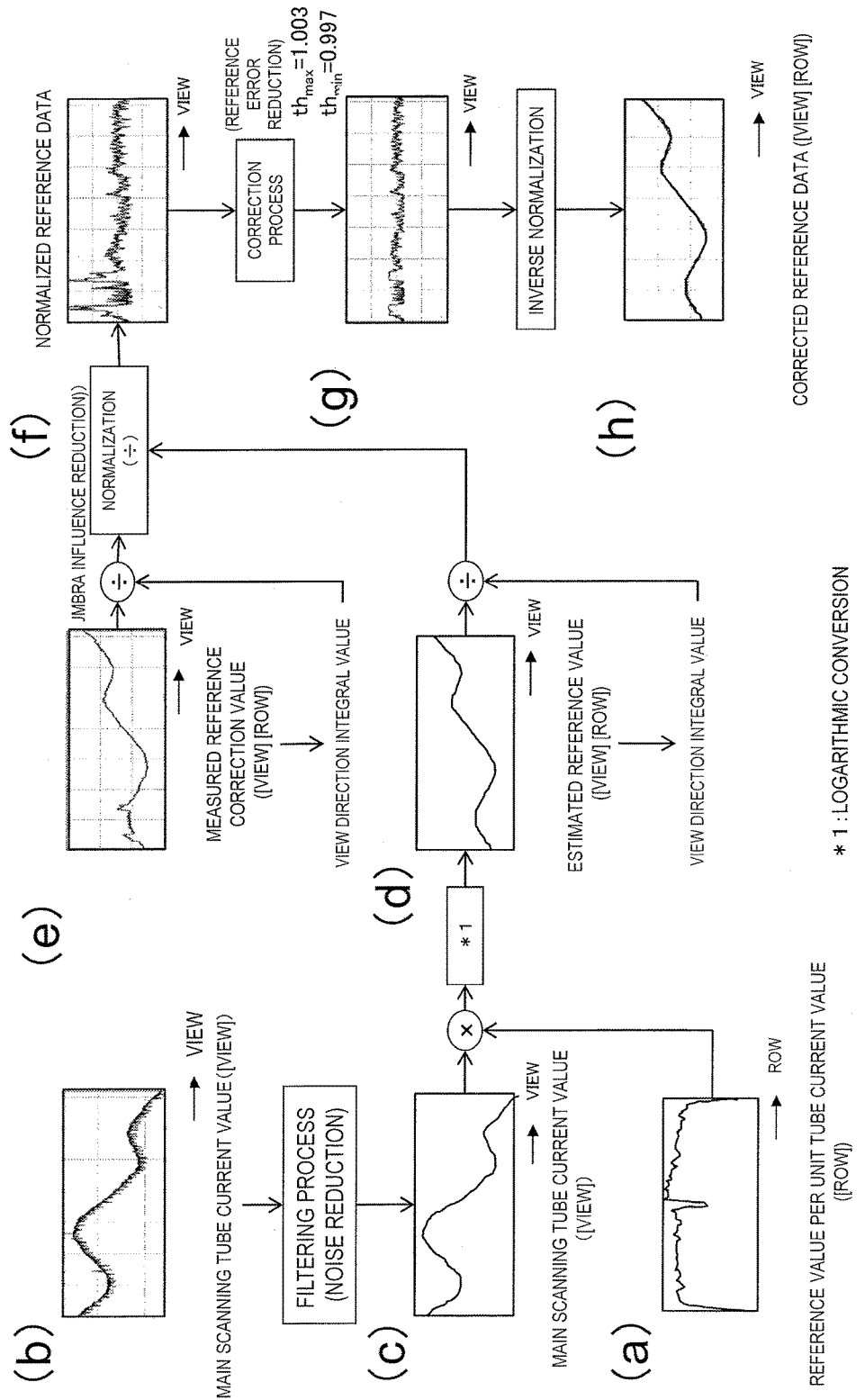
FIG. 6 is a flowchart illustrating procedures of a corrected reference data calculation process.

FIG. 6 (a) is a graph illustrating a reference value per unit tube current (unit air calibration reference value). The unit air calibration reference value is obtained for each detector row.

Next, the X-ray CT apparatus 1 performs main scanning (step S105). In the main scanning, the system control device 124 determines optimal X-ray conditions, and notifies the X-ray control device 110 thereof. The system control device 124 preferably calculates optimal X-ray conditions (a tube current value and a tube voltage value) for each view according to a size or an organ position of the object 3, scanning conditions, and the like. The X-ray control device 110 applies X-rays according to the tube current value and the tube voltage value determined by the system control device 124.

The image processing device 122 acquires X-ray attenuation data detected by the X-ray detector 106 in the main scanning. The image processing device 122 holds the acquired X-ray attenuation data in the storage device 123. The system control device 124 acquires an output tube current value (main scanning tube current value) measured by the tube current measurement device 112 in the main scanning throughout all views, and records the value in the storage device 123 (step S106).

The image processing device 122 preferably reduces noise included in the measured main scanning tube current value. Regarding a specific noise reduction method, for example, a main scanning tube current curve (refer to FIG. 6(b)) in which a main scanning tube current value is recorded for each view is created, and a noise filtering process such as moving average filtering or median filtering is performed on the created main scanning tube current curve in a view direction. If noise of the main scanning tube current value is reduced, it is possible to improve final correction accuracy in reference correction. FIG. 6(b) is a curve (main scanning tube current curve) illustrating the main scanning tube current value obtained in step S106, and FIG. 6(c) is a curve indicating amain scanning tube current value from which noise is reduced.

The image processing device 122 acquires X-ray attenuation data measured by the reference detectors 107 in the main scanning, performs logarithmic conversion on the data, and holds the data in the storage device 123 or the like as a main scanning reference value (step S107). The main scanning reference value is measured by each of the reference detectors 107L and 107R at both ends so as to be held.

Next, the image processing device 122 performs a corrected reference data calculation process of correcting the reference value in the main scanning (step S108).

Figure 7:
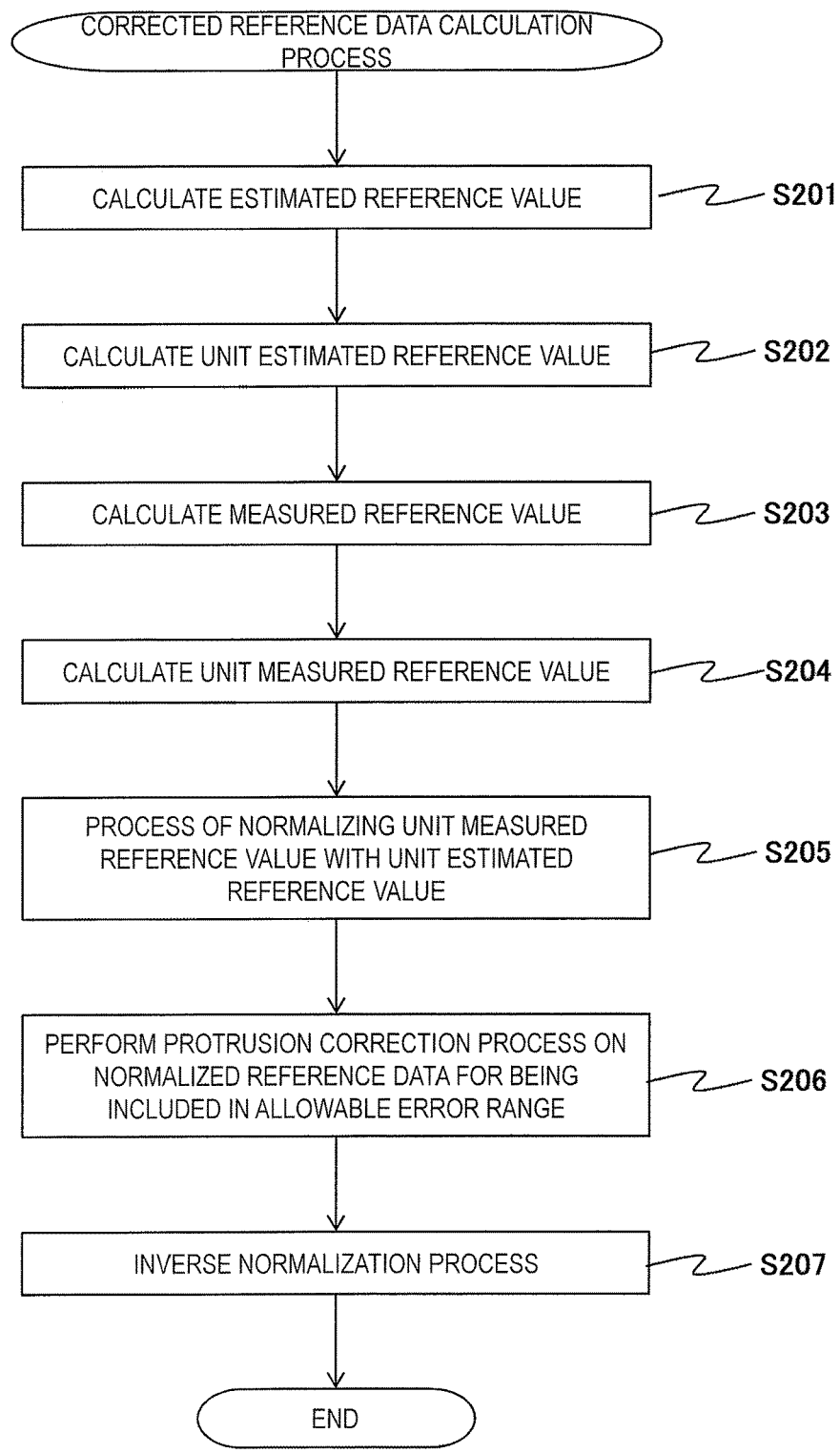
FIG. 7 is a diagram illustrating data profiles in respective steps in the corrected reference data calculation process illustrated in FIG. 6.

FIG. 7 is a flowchart illustrating procedures of the corrected reference data calculation process.

First, the image processing device 122 calculates an "estimated reference value" (step S201).

The estimated reference value is obtained by performing logarithmic conversion on a result obtained by multiplying the "reference value per unit tube current (unit air calibration reference value)" (FIG. 6 (*a*)) obtained during the air calibration by the above-described "main scanning tube current value" (FIG. 6 (c)). In other words, the estimated reference value is obtained according to the following Equation (3).

$$\text{Estimated reference value} = -\log(\text{main scanning tube current value} * \text{unit air calibration reference value}) \quad (3)$$

The estimated reference value is a value obtained by converting the unit air calibration reference value measured during the air calibration (a state in which there is no object) into an X-ray condition (main scanning tube current value) in the main scanning. FIG. 6(*d*) is a graph illustrating a view direction change in the estimated reference value. The estimated reference value is obtained for each row.

Next, the image processing device 122 integrates the estimated reference values obtained in step S201 in the view direction, and normalizes the estimated reference values by dividing the estimated reference values by an integral value (step S202). The normalized estimated reference value is referred to as a "unit estimated reference value". The integration mentioned here maybe averaging, and may be moving averaging using peripheral data of a view position which is a normalization target.

Next, the image processing device 122 calculates a measured reference value (step S203).

The measured reference value is obtained on the basis of the main scanning reference values (step S107) measured by both of the reference detectors 107L and 107R in the main scanning.

As methods of calculating a measured reference value, the following methods (A) to (D) may be employed.

(A) A method of calculating an average value (an average value for each view) of measured values in the reference detectors 107L and 107R at both ends and using the calculated average value as a measured reference value.

(B) A method of performing determination of object protrusion for each view by using a difference between measured values in the reference detectors 107L and 107R at both ends, and using a measured value in a reference detector in which there is no protrusion in a case where the object 3 protrudes in either one thereof as a measured reference value.

(C) A method of performing determination of object protrusion on the basis of a difference between the measured reference value calculated in the above-described method (A) or (B) and a measured reference value for the previous view, determining that both sides of the object 3 protrude in a case where the difference from the measured reference value for the previous view is great, and the value is greater than the value for the previous view, and using the reference value for the previous view as a measured reference value.

(D) A method of performing determination of object protrusion on the basis of a difference between the measured reference value calculated in the above-described method (A) or (B) and a measured reference value for the previous view, determining that both sides of the object 3 protrude in a case where the difference from the measured reference value for the previous view is great, and the value is greater than the value for the previous view, and using the estimated reference value calculated in step S201 as a measured reference correction value.

A measured reference value is not limited to being obtained according to the above methods (A) to (D), and may be obtained according to any method. According to the above-described methods, in both ends of the detector, threshold values Th_LR for left-and-right comparison or threshold values Th_FE for previous-and-following comparison, set in advance, are used for comparison with projection values at both ends or projection values for the previous and following views. The threshold values Th_LR and Th_FE are used to differentiate a projection value change due to noise on projection data from a projection value change due to protrusion. Thus, for example, in a case where there is object protrusion on one side, but a difference between projection values for both ends of the detector is less than the above-described threshold value, the influence of the object protrusion remains as an error.

FIG. 6(*e*) shows a curve (measured reference data) indicating a view direction change in a measured reference value. The measured reference data is recorded for each row.

The image processing device 122 integrates the measured reference values obtained in step S203 in the view direction, and calculates a unit measured reference value by dividing the measured reference values by an integral value (step S204). The integration mentioned here may be averaging, and may be moving averaging using peripheral data of a view position which is a normalization target.

Next, the image processing device 122 normalizes the unit measured reference value obtained in step S204 with the unit estimated reference value obtained in step S202 (step S205). Specifically, the image processing device 122 calculates a normalized reference data by dividing the unit measured reference value by the unit estimated reference value.

Since the unit measured reference value or the unit estimated reference value obtained through division using the view direction integral value is used as described above when the normalized reference data is calculated, it is possible to reduce the influence of a penumbra effect caused by a difference between focal point positions of the X-ray tube in air scanning and main scanning.

The normalized reference data is a value close to "1" in a case where there is no object protrusion, and is a value which is considerably deviated from "1" in a case where there is object protrusion, as illustrated in FIG. 6(*f*).

Next, the image processing device 122 performs a protrusion correction process on the normalized reference data (step S206). In other words, a threshold value determination is performed on the normalized reference data by using a reference range (an upper limit threshold value $th_{max}$ and a lower limit threshold value $th_{min}$) set in advance, and a value which is equal to or greater than the upper limit threshold value $th_{max}$, and a value which is equal to or smaller than the lower limit threshold value $th_{min}$ are corrected to be included in the reference range. For example, a value which is equal to or greater than the upper limit threshold value $th_{max}$ is replaced with the upper limit threshold value $th_{max}$, and a value which is equal to or smaller than the lower limit threshold value $th_{min}$ is replaced with the lower limit threshold value $th_{min}$.

In the example illustrated in FIG. 6, the upper limit threshold value $th_{max}$ is "1.003", and the lower limit threshold value $th_{min}$ is "0.997". The reference range (the upper limit threshold value $th_{max}$ and the lower limit threshold value $th_{min}$) may be set to values corresponding to X-ray conditions.

A value which is equal to or greater than the upper limit threshold value $th_{max}$ may be replaced with an interpolation value obtained by using normalized reference data adjacent to the value which is equal to or greater than the upper limit threshold value $th_{max}$ in the view direction. Similarly, a value which is equal to or smaller than the lower limit threshold value $th_{min}$ may be replaced with an interpolation value obtained by using normalized reference data adjacent to the value which is equal to or smaller than the lower limit threshold value $th_{min}$ in the view direction.

Consequently, as illustrated in FIG. 6 (g), the normalized reference data is corrected to a value close to "1" throughout all views. In other words, it is possible to obtain normalized reference data from which the influence of protrusion is removed and which thus indicates a component regarding a change in an inherent X-ray output.

Next, the normalized reference data having undergone the protrusion correction is inversely normalized by using the unit estimated reference value obtained in step S202 (step S207). Specifically, the normalized reference data having undergone the protrusion correction is multiplied by normalization estimated reference data. Consequently, corrected reference data as illustrated in FIG. 6(h) is calculated.

Through the above-described series of processes, it is possible to obtain corrected reference data in which the influence of protrusion is removed from reference data measured in a state in which object protrusion occurs, and X-ray conditions in main scanning or a component regarding an X-ray output change remains.

The image processing device 122 performs reference correction on the projection data obtained in the main scanning by using the corrected reference data obtained in step S207 (step S109 in FIG. 5).

In the reference correction, the image processing device 122 subtracts the corrected reference data obtained in step S207 from the projection data obtained in the main scanning for each view.

As described above, through the corrected reference data calculation process of the present embodiment, it is possible to obtain corrected reference data in which the influence of object protrusion is removed from reference data in main scanning, and X-ray conditions in the main scanning or a component regarding an X-ray output change remains. If reference correction is performed on projection data by using such corrected reference data, it is possible to perform highly accurate reference correction even in a case where protrusion of an object occurs in most of the views or a case where protrusion occurs from the first view.

[Second Embodiment]

Next, with reference to FIGS. 8 and 9, a second embodiment of the present invention will be described.

A configuration of an X-ray CT apparatus 1 according to the second embodiment is the same as that in the first embodiment. Hereinafter, repeated description will be omitted, and the same constituent elements are given the same reference signs.

In the second embodiment, a description will be made of a case where reference correction is performed on measured data (X-ray attenuation data) not having undergone logarithmic conversion. Approximate procedures of a projection data generation process are the same as those in the first embodiment, and thus the process will be described with reference to the flowchart illustrated in FIG. 5.

In the same manner as in the first embodiment, the X-ray CT apparatus 1 first performs air calibration prior to main scanning, so as to record an output tube current value (air scanning tube current value) during the air scanning, acquires X-ray attenuation data measured by the reference detectors 107 in the air scanning, and holds the X-ray attenuation data in the storage device 123 or the like as an air calibration reference value (steps S101 to S103 in FIG. 5). The image processing device 122 calculates a "reference value per unit tube current (1 mA) (unit air calibration reference value)" on the basis of the recorded air scanning tube current value and the air calibration reference value, and holds the unit air calibration reference value in the storage device 123 (step S104 in FIG. 5).

Next, the X-ray CT apparatus 1 performs main scanning (step S105). The image processing device 122 acquires X-ray attenuation data detected by the X-ray detector 106 in the main scanning. The image processing device 122 holds the acquired X-ray attenuation data in the storage device 123. The system control device 124 acquires an output tube current value (main scanning tube current value) measured by the tube current measurement device 112 in the main scanning throughout all views, and records the value in the storage device 123 (step S106). The image processing device 122 preferably reduces noise included in the main scanning tube current value.

The image processing device 122 acquires X-ray attenuation data measured by the reference detectors 107 in the main scanning, and holds data not having undergone logarithmic conversion in the storage device 123 or the like as a main scanning reference value (step S107). The main scanning reference value is measured by each of the reference detectors 107L and 107R at both ends so as to be held.

Next, the image processing device 122 performs a corrected reference data calculation process of correcting the reference value (not having undergone logarithmic conversion) in the main scanning (step S108).

Figure 8:
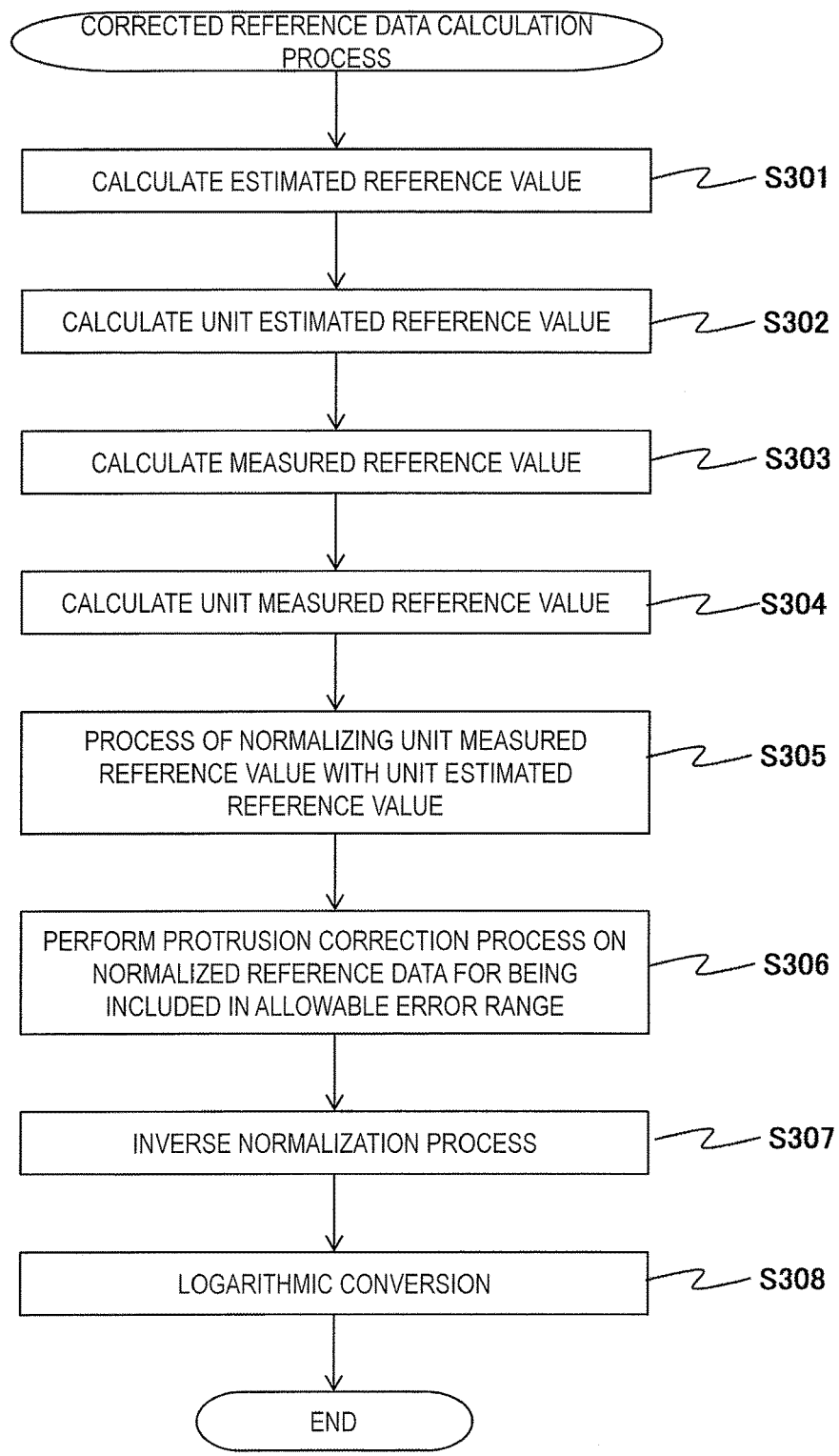
FIG. 8 is a flowchart illustrating procedures of a corrected reference data calculation process.

FIG. 8 is a flowchart illustrating procedures of a corrected reference data calculation process using data not having undergone logarithmic conversion.

First, the image processing device 122 calculates an "estimated reference value" (step S301).

The estimated reference value is obtained by multiplying the "reference value per unit tube current" (FIG. 9(a)) obtained during the air calibration by the above-described "main scanning tube current value" (FIG. 9(c)). In other words, the estimated reference value is obtained according to the following Equation (4). The second embodiment is different from the first embodiment in that logarithmic conversion is not performed in this step.

Estimated reference value=main scanning tube current value*reference value per unit tube current (4)

FIG. 9(d) is a graph illustrating a view direction change in the estimated reference value (not having undergone logarithmic conversion) in the second embodiment. The estimated reference value is obtained for each row.

Next, the image processing device 122 integrates the estimated reference values obtained in step S301 in the view direction, and normalizes the estimated reference values by dividing the estimated reference values by an integral value (step S302). The normalized estimated reference value is referred to as a unit estimated reference value.

Next, the image processing device 122 calculates a measured reference value (step S303).

The measured reference value is obtained on the basis of the main scanning reference values (step S107) measured by both of the reference detectors 107L and 107R in the main scanning. The second embodiment is different from the first embodiment in that X-ray attenuation data not having undergone logarithmic conversion is used.

The measured reference value is preferably calculated by using, for example, any one of the above-described methods (A) to (D).

FIG. 9(e) shows a curve (measured reference data) indicating a view direction change in a measured reference value not having undergone logarithmic conversion. The measured reference data is recorded for each row.

The image processing device 122 integrates the measured reference values obtained in step S303 in the view direction, and calculates a unit measured reference value by dividing the measured reference values by an integral value (step S304). The integration mentioned here may be averaging, and may be moving averaging using peripheral data of a view position which is a normalization target.

Next, the image processing device 122 normalizes the unit measured reference value obtained in step S304 with the unit estimated reference value obtained in step S302 (step S305). Specifically, the image processing device 122 calculates normalized reference data by dividing the unit measured reference value by the unit estimated reference value.

As illustrated in FIG. 9(f), the normalized reference data is a value close to "1" in a case where there is no object protrusion, and is a value which is considerably deviated from "1" in a case where there is object protrusion.

Next, the image processing device 122 performs a protrusion correction process on the normalized reference data (step S306). In other words, a threshold value determination is performed on the normalized reference data by using a reference range (an upper limit threshold value $th_{max}$ and a lower limit threshold value $th_{min}$) set in advance, and a value which is equal to or greater than the upper limit threshold value $th_{max}$ and a value which is equal to or smaller than the lower limit threshold value $th_{min}$ are corrected to be included in the reference range. For example, a value which is equal to or greater than the upper limit threshold value $th_{max}$ is replaced with the upper limit threshold value $th_{max}$, and a value which is equal to or smaller than the lower limit threshold value $th_{min}$ is replaced with the lower limit threshold value $th_{min}$.

In FIG. 9, the upper limit threshold value $th_{max}$ is "1.03", and the lower limit threshold value $th_{min}$ is "0.97". The normalized reference data calculated by using the data not having undergone logarithmic conversion is more irregular than in the first embodiment, and thus a wider reference range is used.

Consequently, as illustrated in FIG. 9 (g), the normalized reference data is corrected to a value close to "1" throughout all views. In other words, it is possible to obtain normalized reference data from which the influence of protrusion is removed and which thus a component regarding a change in an inherent X-ray output remains.

Next, the normalized reference data having undergone the protrusion correction is inversely normalized by using the unit estimated reference value obtained in step S302 (step S307). Specifically, the inverse normalization indicates that the normalized reference data having undergone the protrusion correction is multiplied by normalization estimated reference data. Consequently, corrected reference data as illustrated in FIG. 9(h) is calculated.

The image processing device 122 performs reference correction on the X-ray attenuation data obtained in the main scanning by using the corrected reference data (not having undergone logarithmic conversion) obtained in step S307 (step S109 in FIG. 5). In the reference correction, the image processing device 122 divides the X-ray attenuation data obtained in the main scanning by the corrected reference data obtained in step S307 for each view.

If logarithmic conversion is performed on the corrected reference data (FIG. 9(h)) obtained in step S307, corrected reference data having undergone the logarithmic conversion can be obtained in the same manner as in the first embodiment as illustrated in FIG. 9(i) (step S308).

As described above, through the corrected reference data calculation process of the present embodiment, it is possible to obtain corrected reference data in which the influence of object protrusion is removed from reference data in main scanning, and X-ray conditions in the main scanning or a component regarding an X-ray output change remains. If reference correction is performed on projection data by using such corrected reference data, it is possible to perform highly accurate reference correction even in a case where protrusion of an object occurs in most of the views or a case where protrusion occurs from the first view.

When compared with the first embodiment with the second embodiment, normalized reference data (FIG. 6(g)) having undergone logarithmic conversion has a smaller data variation, more easily manifests the influence of protrusion, and more easily removes the influence of protrusion. In other words, even if an allowable error range in protrusion correction in step S206 is narrower, a component caused by protrusion can be sufficiently removed. Thus, the corrected reference data obtained according to the procedures of the first embodiment is closer to data which is actually measured in main scanning than the corrected reference data obtained according to the procedures of the second embodiment. Therefore, if reference correction is performed by using the data, an artifact or the like can be reduced.

Even if the above-described projection data generation method of each embodiment is applied to measured data (projection data or X-ray attenuation data) obtained when protrusion does not occur, a sufficient effect can be achieved.

The measured reference value in FIG. 6(e) is not used, but the estimated reference value in FIG. 6(d) may be treated as corrected reference data. As mentioned above, the preferred embodiments of the X-ray CT apparatus and the like according to the present invention have been described, but the present invention is not limited to the above-described embodiments. It is clear that a person skilled in the art can conceive of various modifications or alterations within the technical spirit disclosed in the present specification, and it is understood that they are naturally included in the technical scope of the present invention.

REFERENCE SIGNS LIST

1 X-RAY CT APPARATUS, 100 SCAN GANTRY UNIT, 101 X-RAY SOURCE, 102 ROTATION BOARD, 103 COLLIMATOR, 106 X-RAY DETECTOR, 107R AND 107L REFERENCE DETECTORS, 111 X-RAY CONTROL DEVICE, 112 TUBE CURRENT MEASUREMENT DEVICE, 120 OPERATION CONSOLE, 121 INPUT DEVICE, 122 IMAGE PROCESSING DEVICE (DATA PROCESSING DEVICE), 123 STORAGE DEVICE, 124 SYSTEM CONTROL DEVICE, 125 DISPLAY DEVICE

The invention claimed is:
1. A data processing device comprising:
a unit air calibration reference value calculation unit that calculates a unit air calibration reference value which is a value per unit tube current of an air calibration reference value corresponding to reference data measured during air calibration;
a tube current value acquisition unit that acquires an output tube current value in main scanning;

an estimated reference value calculation unit that calculates an estimated reference value corresponding to an X-ray condition in the main scanning on the basis of the unit air calibration reference value and the output tube current value in the main scanning;
a normalization unit that normalizes a measured reference value measured in the main scanning with the estimated reference value, so as to calculate normalized reference data;
a correction processing unit that corrects the normalized reference data, to be included in an allowable error range;
an inverse normalization unit that inversely normalizes the corrected normalized reference data with the estimated reference value so as to obtain corrected reference data; and
a reference correction unit that acquires measured data, which is measured in the main scanning, and performs reference correction on the measured data by using the corrected reference data.

2. The data processing device according to claim 1, further comprising:
a noise removal unit that removes noise from the output tube current value,
wherein the estimated reference value calculation unit calculates the estimated reference value by using the output tube current value from which noise is removed.

3. The data processing device according to claim 1, wherein the normalization unit
normalizes the measured reference value with an integral value obtained by integrating the measured reference value in a view direction, so as to obtain a unit measured reference value;
normalizes the estimated reference value with an integral value obtained by integrating the estimated reference value in the view direction, so as to obtain a unit estimated reference value; and
normalizes the unit measured reference value with the unit estimated reference value so as to calculate the normalized reference data.

4. The data processing device according to claim 1, wherein the measured reference value and the estimated reference value are values having undergone logarithmic conversion.

5. The data processing device according to claim 1, wherein the measured reference value and the estimated reference value are values not having undergone logarithmic conversion.

6. The data processing device according to claim 1, wherein an allowable error used in the correction processing unit is set according to X-ray conditions of the main scanning.

7. An X-ray CT apparatus comprising the data processing device according to claim 1.

8. A reference correction method comprising:
causing a data processing device to perform
a step of calculating a unit air calibration reference value which is a value per unit tube current of an air calibration reference value measured during air calibration;
a step of acquiring an output tube current value in main scanning;
a step of calculating an estimated reference value corresponding to an X-ray condition in the main scanning on the basis of the unit air calibration reference value and the output tube current value in the main scanning;
a step of normalizing a measured reference value measured in the main scanning with the estimated reference value, so as to calculate normalized reference data;
a step of correcting the normalized reference data, to be included in an allowable error range;
a step of inversely normalizing the corrected normalized reference data with the estimated reference value so as to obtain corrected reference data; and
a step of acquiring measured data, which is measured in the main scanning, and performing reference correction on the measured data by using the corrected reference data.

* * * * *